United States Patent
Rioux et al.

(10) Patent No.: US 7,354,436 B2
(45) Date of Patent: *Apr. 8, 2008

(54) SYSTEMS AND METHODS FOR PERFORMING SIMULTANEOUS ABLATION

(75) Inventors: Robert F. Rioux, Ashland, MA (US); Robert Garabedian, Tyngsboro, MA (US); Jerry Jarrard, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/238,403

(22) Filed: Sep. 28, 2005

(65) Prior Publication Data

US 2006/0025764 A1 Feb. 2, 2006

Related U.S. Application Data

(63) Continuation of application No. 10/713,357, filed on Nov. 14, 2003, now Pat. No. 6,958,064.

(51) Int. Cl.
*A61B 18/18* (2006.01)
*A61B 18/14* (2006.01)

(52) U.S. Cl. .......................................... 606/32; 606/41

(58) Field of Classification Search .................. 606/41, 606/42, 45–50; 607/100–102; 604/21, 22, 604/1

See application file for complete search history.

(56) References Cited

U.S. PATENT DOCUMENTS 4,071,028 A 1/1978 Perkins
5,817,092 A 10/1998 Behl
5,855,576 A 1/1999 LeVeen et al.

(Continued)

FOREIGN PATENT DOCUMENTS

WO WO 99/04710 2/1999

(Continued)

OTHER PUBLICATIONS

PCT International Search Report for PCT/US2004/036479, Applicant: Scimed Life Systems, Inc., Forms PCT/ISA/210 and 220, dated Feb. 8, 2005 (7 pages).

(Continued)

*Primary Examiner*—Lee S. Cohen
(74) *Attorney, Agent, or Firm*—Vista IP Law Group LLP

(57) ABSTRACT

A system for treating tissue includes first and second ablation devices each including a plurality of wire electrodes and coupled to a generator in parallel. In one embodiment, the generator includes first and second terminals coupled in parallel to one another, and the first and second ablation devices are connected to the first and second terminals, respectively. Alternatively, the first and second ablation devices are coupled to a single terminal of the generator using a "Y" cable. A ground electrode is coupled to the generator opposite the first and second ablation devices for monopolar operation. The first and second arrays of electrodes are inserted into first and second sites adjacent one another within a tissue region. Energy is simultaneously delivered to the first and second arrays to generate lesions at the first and second sites preferably such that the first and second lesions overlap.

24 Claims, 4 Drawing Sheets

U.S. PATENT DOCUMENTS

| | | | |
|---|---|---|---|
| 5,951,547 A * | 9/1999 | Gough et al. | 606/41 |
| 6,080,149 A | 6/2000 | Huang et al. | |
| 6,132,425 A | 10/2000 | Gough | |
| 6,337,998 B1 * | 1/2002 | Behl et al. | 606/41 |
| 6,575,967 B1 * | 6/2003 | Leveen et al. | 606/41 |
| 6,958,064 B2 * | 10/2005 | Rioux et al. | 606/41 |
| 6,979,330 B2 * | 12/2005 | Kelly et al. | 606/41 |
| 2001/0007939 A1 | 7/2001 | Fleishman | |
| 2002/0156472 A1 | 10/2002 | Lee et al. | |
| 2003/0195502 A1 | 10/2003 | Garabedian et al. | |

FOREIGN PATENT DOCUMENTS

| | | |
|---|---|---|
| WO | WO 00/06046 | 2/2000 |

OTHER PUBLICATIONS

PCT Written Opinion of the International Search Authority for PCT/US2004/036479, Applicant: Scimed Life Systems, Inc., Form PCT/ISA/237, dated Feb. 8, 2005 (4 pages).

* cited by examiner

SYSTEMS AND METHODS FOR PERFORMING SIMULTANEOUS ABLATION

CROSS-REFERENCE TO RELATED APPLICATIONS

This application is a continuation of U.S. application Ser. No. 10/713,357, filed on Nov. 14, 2003, now U.S. Pat. No. 6,958,064, the disclosures of which is hereby incorporated herein by reference in their entirety.

BACKGROUND OF THE INVENTION

1. Field of the Invention

The field of the invention relates to medical devices, and more particularly, to systems and methods for ablating or otherwise treating tissue using electrical energy.

2. Background of the Invention

Tissue may be destroyed, ablated, or otherwise treated using thermal energy during various therapeutic procedures. Many forms of thermal energy may be imparted to tissue, such as radio frequency electrical energy, microwave electromagnetic energy, laser energy, acoustic energy, or thermal conduction.

In particular, radio frequency ablation (RFA) may be used to treat patients with tissue anomalies, such as liver anomalies and many primary cancers, such as cancers of the stomach, bowel, pancreas, kidney and lung. RFA treatment involves the destroying undesirable cells by generating heat through agitation caused by the application of alternating electrical current (radio frequency energy) through the tissue.

Various RF ablation devices have been suggested for this purpose. For example, U.S. Pat. No. 5,855,576 describes an ablation apparatus that includes a plurality of wire electrodes deployable from a cannula or catheter. Each of the wires includes a proximal end that is coupled to a generator, and a distal end that may project from a distal end of the cannula. The wires are arranged in an array with the distal ends located generally radially and uniformly spaced apart from the catheter distal end. The wires may be energized in a monopolar or bipolar configuration to heat and necrose tissue within a precisely defined volumetric region of target tissue. The current may flow between closely spaced wire electrodes (bipolar mode) or between one or more wire electrodes and a larger, common electrode (monopolar mode) located remotely from the tissue to be heated. To assure that the target tissue is adequately treated and/or to limit damaging adjacent healthy tissues, the array of wires may be arranged uniformly, e.g., substantially evenly and symmetrically spaced-apart so that heat is generated uniformly within the desired target tissue volume. Such devices may be used either in open surgical settings, in laparoscopic procedures, and/or in percutaneous interventions.

During tissue ablation, the maximum heating often occurs in the tissue immediately adjacent the emitting electrodes. In general, the level of tissue heating is proportional to the square of the electrical current density, and the electrical current density in tissue generally falls rapidly with increasing distance from the electrode. The decrease of a current density depends upon a geometry of the electrode. For example, if the electrode has a spherical shape, the current density will generally fall as the second power of distance from the electrode. On the other hand, if the electrode has an elongate shape (e.g., a wire), the current density will generally fall with distance from the electrode, and the associated power will fall as the second power of distance from the electrode. For the case of spherical electrode, the heating in tissue generally falls as the fourth power of distance from the electrode, and the resulting tissue temperature therefore decreases rapidly as the distance from the electrode increases. This causes a lesion to form first around the electrodes, and then to expand into tissue disposed further away from the electrodes.

Due to physical changes within the tissue during the ablation process, the size of the lesion created may be limited. For example, the concentration of heat adjacent to wires often causes the local tissue to desiccate, thereby reducing its electrical conductivity. As the tissue conductivity decreases, the impedance to current passing from the electrode to the tissue increases so that more voltage must be supplied to the electrodes to affect the surrounding, more distant tissue. The tissue temperature proximate to the electrode may approach 100° C., so that water within the tissue boils to become water vapor. As this desiccation and/or vaporization process continues, the impedance of the local tissue may rise to the point where a therapeutic level of current can no longer pass through the local tissue into the surrounding tissue.

Thus, the rapid fall-off in current density may limit the volume of tissue that can be treated by the wire electrodes. As such, depending upon the rate of heating and the size of the wire electrodes, existing ablation devices may not be able to create lesions that are relatively large in size. Longer wire electrodes and/or larger arrays have been suggested for creating larger lesions. The effectiveness of such devices, however, may be limited by the desiccation and/or vaporization process discussed previously. While wire electrodes can be deployed, activated, retracted, and repositioned sequentially to treat multiple locations within a tissue region, such an approach may increase the length of time of a procedure, and precise positioning to ensure that an entire tissue region is treated may be difficult to accomplish.

Accordingly, improved systems and methods for tissue ablation would be useful.

SUMMARY OF THE INVENTION

The present invention is directed to systems and methods for delivering energy to tissue, and more particularly to systems and methods for delivering energy substantially simultaneously to multiple electrode arrays to increase a volume of tissue being treated.

In accordance with a first aspect of the present invention, a system for treating tissue within a tissue region is provided that includes a source of energy, a first ablation device including a plurality of wires coupled to the source of energy, and a second ablation device including a plurality of wires coupled to the source of energy in parallel with the first ablation device, whereby the first and second ablation devices can substantially simultaneously create first and second lesions, respectively, within a tissue region.

In a preferred embodiment, the wires of the first and second ablation devices are electrodes and the source of energy is a source of electrical energy, e.g., a radio frequency (RF) generator. Preferably, the first and second ablation devices include an array of wires deployable from a cannula.

The source of electrical energy may include first and second terminals coupled in parallel to one another. The first ablation device may be coupled to the first terminal and the second ablation device may be coupled to the second terminal. Alternatively, the source of electrical energy may include a terminal, and a "Y" cable or other connector may be coupled between the first and second ablation devices and the terminal to couple the first and second ablation devices in parallel. Optionally, a ground electrode may be coupled to the source of energy opposite the first and second ablation devices, e.g., to provide a return path for electrical energy delivered to the tissue from the electrodes.

In accordance with another aspect of the present invention, a method is provided for creating a lesion within a tissue region, e.g., a benign or cancerous tumor within a liver or other tissue structure. A first array of electrodes may be inserted into a first site within the tissue region, and a second array of electrodes may be inserted into a second site within the tissue region. Preferably, the second array of electrodes is coupled in parallel with the first array of electrodes, e.g., to a RF generator or other source of energy.

In one embodiment, the first and second arrays of electrodes may be introduced into the first and second sites from first and second cannulas, respectively. Preferably, the first and second cannulas are introduced into the tissue region until distal ends of the first and second cannulas are disposed adjacent the first and second sites, respectively. The first and second arrays of electrodes may then be deployed from the distal ends of the first and second cannulas into the first and second sites, respectively.

Energy may be substantially simultaneously delivered to the first and second arrays of electrodes to generate lesions at the first and second sites within the tissue region. Preferably, the first and second sites are disposed adjacent to one another within the tissue region such that the first and second lesions at least partially overlap. Optionally, at least one or both of the first and second arrays of electrodes may be removed from the tissue region and introduced into a third (and fourth) site within the tissue region, and activated to increase the size of the lesion created. In other embodiments, the first and second arrays of electrodes can be placed at different sites, each of which is associated with a treatment region. In such arrangement, separate tissues at different treatment sites can be ablated simultaneously.

Other aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting its scope, the invention will be described and explained with additional specificity and detail through the use of the accompanying drawings.

DETAILED DESCRIPTION OF THE PREFERRED EMBODIMENTS

Figure 1:
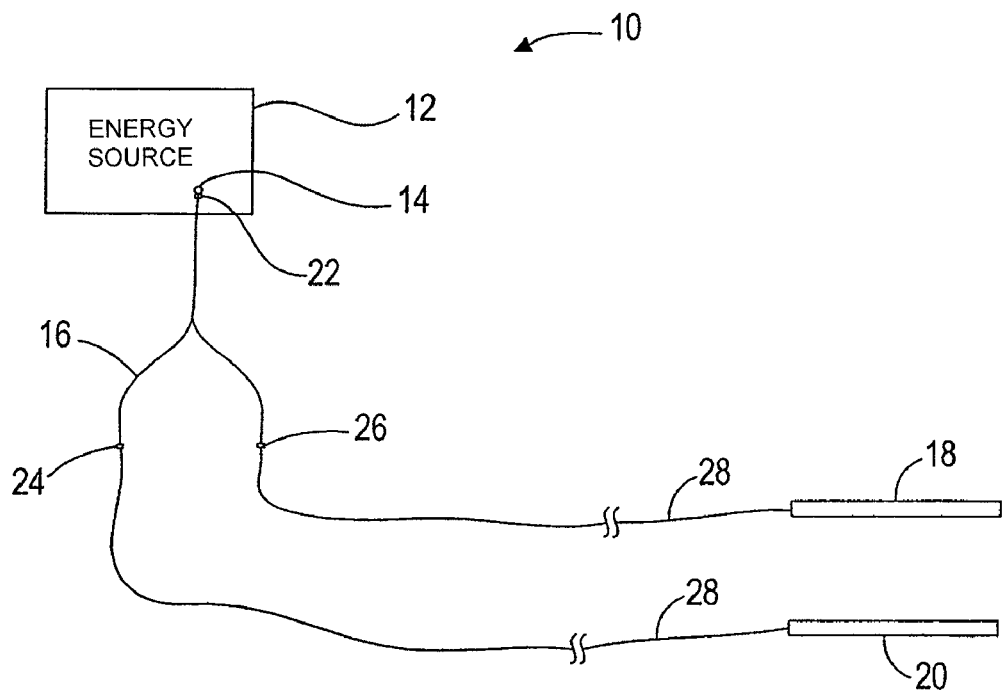
FIG. 1 illustrates a system for delivering electrical energy to tissue, in accordance with a preferred embodiment of the present invention.

Referring now to the drawings, in which similar or corresponding parts are identified with the same reference numeral, FIG. 1 shows a preferred embodiment of an ablation system 10, in accordance with the present invention. The ablation system 10 includes a source of energy 12, e.g., a radio frequency (RF) generator, having an output terminal 14, a connector 16, a first ablation device 18, and a second ablation device 20. One or both of the first and the second ablation devices 18, 20 may be capable of being coupled to the generator 12.

The generator 12 is preferably capable of operating with a fixed or controlled voltage so that power and current diminish as impedance of the tissue being ablated increases. Exemplary generators are described in U.S. Pat. No. 6,080,149, the disclosure of which is expressly incorporated by reference herein. The preferred generator 12 may operate at relatively low fixed voltages, typically below one hundred fifty volts (150 V) peak-to-peak, and preferably between about fifty and one hundred volts (50-100 V). Such radio frequency generators are available from Boston Scientific Corporation, assignee of the present application, as well as from other commercial suppliers. It should be noted that the generator 12 is not limited to those that operate at the range of voltages discussed previously, and that generators capable of operating at other ranges of voltages may also be used.

The connector 16 includes an input terminal 22, a first output terminal 24, and a second output terminal 26 that is connected in parallel with the first output terminal 24. The first and second output terminals 24 and 26 of the connector 16 are configured for coupling to the first and second ablation devices 18, 20, respectively, while the input terminal 22 of the connector 16 is configured for coupling to the output terminal 14 of the generator 12. Optionally, the ablation system 10 may include one or more cables 28, e.g., extension cables or cables that extend from the first and second ablation devices 18, 20. If cables 28 are not provided, the first and second ablation devices 18, 20 may be coupled directly to the output terminals 24 and 26, respectively, of the connector 16. In the illustrated embodiment, the connector 16 may deliver power from the generator 12 simultaneously to the first and second ablation devices 18, 20. If it is desired to deliver power to more than two ablation devices, the connector 16 may have more than two output terminals connected in parallel to one another (not shown).

Figure 2:
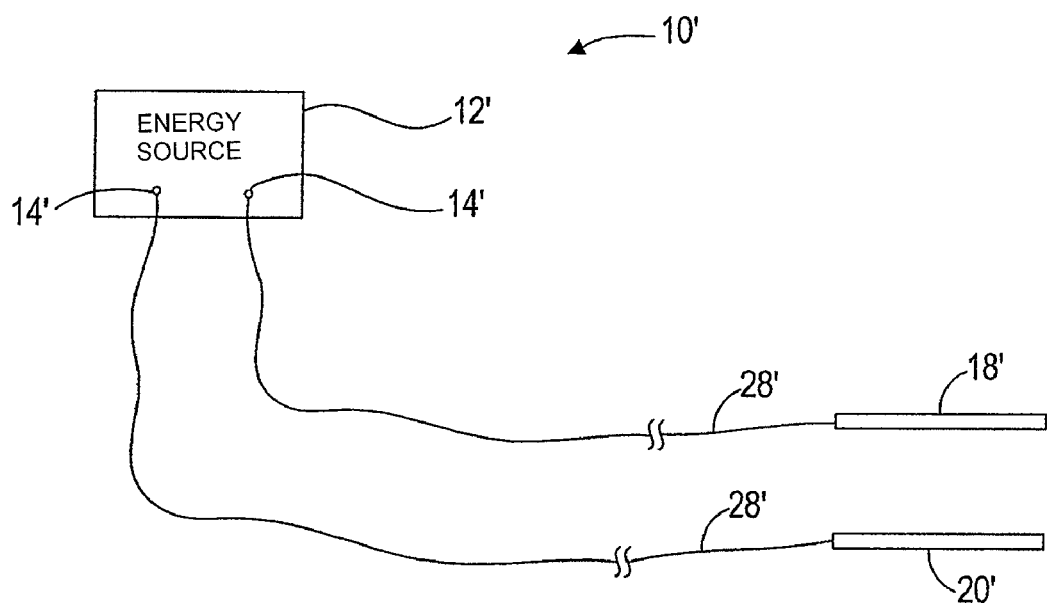
FIG. 2 illustrates a variation of the ablation system of FIG. 1, showing the power supply having a plurality of output terminals.

Alternatively, as shown in FIG. 2, instead of the "Y" connector 16, a generator 12' may be provided that includes two (or optionally more) output terminals 14' coupled in parallel with one another. In this case, first and second ablation devices 18,' 20' may be coupled to separate output terminals 14' of the generator 12' without requiring a connector 16 (not shown, see FIG. 1). However, if the generator 12' does not provide an adequate number of output terminals 14 for the number of ablation devices desired, one or more connectors 16 (not shown) may be used to couple two or more ablation devices to a single output terminal of the generator 12.'

The output terminals 14' of the generator 12' may be coupled to common control circuits (not shown) within the generator 12.' Alternatively, the generator 12' may include separate control circuits coupled to each of the output terminals 14.' The control circuits may be connected in parallel with one another, yet may include separate impedance feedback to control energy delivery to the respective output terminals 14.' Thus, the output terminals 14' may be connected in parallel to an active terminal of the generator 12' such that the ablation devices 18,' 20' deliver energy to a common ground pad electrode (not shown) in a monopolar mode. Alternatively, the output terminals 14' may be connected to opposite terminals of the generator 12' for delivering energy between the ablation devices 18,' 20' in a bipolar mode.

Figure 3:
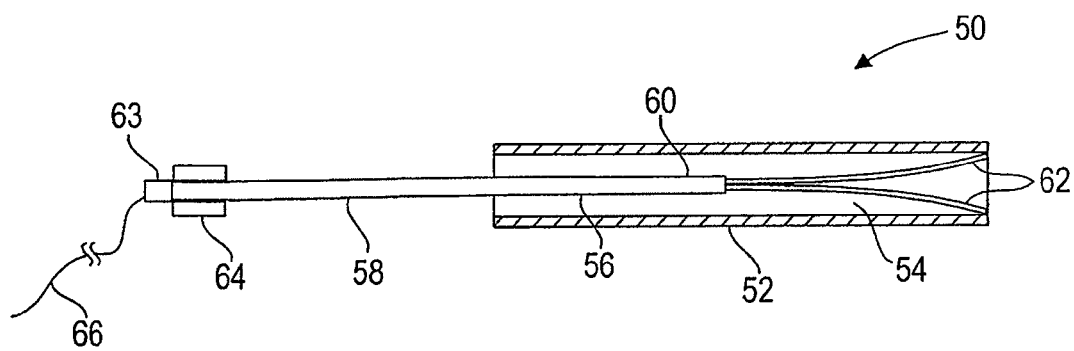
FIG. 3 is a cross-sectional side view of an embodiment of an ablation device, showing electrode wires constrained within a cannula.
Figure 4:
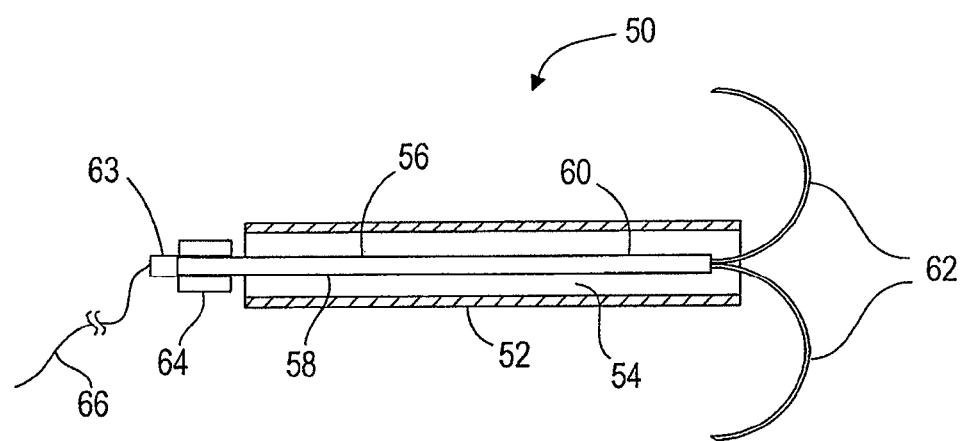
FIG. 4 is a cross-sectional side view of the ablation device of FIG. 3, showing the wires deployed from the cannula.

Turning to FIGS. 3 and 4, in a preferred embodiment, each of the ablation devices 18, 20 of FIG. 1 (or alternatively, the ablation devices 18,' 20' of FIG. 2) may be a probe assembly 50. The probe assembly 50 may include a cannula 52 having a lumen 54, a shaft 56 having a proximal end 58 and a distal end 60, and a plurality of electrode wires 62 secured to the distal end 60 of the shaft 56. The proximal end 58 of the shaft 56 may include a connector 63 for coupling to the generator 12. For example, the connector 62 may be used to connect the probe assembly 50 to a cable 66, which may be part of the connector 16 (not shown, see FIG. 1), an extension cable, or a cable that extends from the output terminal 14 of the generator 12. Alternatively, the probe assembly 50 may itself include a cable (not shown) on the proximal end 58 of the shaft 56, and a connector may be provided on the proximal end of the cable (not shown).

The cannula 52 may have a length between about five and thirty centimeters (5-30 cm), and/or an outer diameter or cross sectional dimension between about one and five millimeters (1-5 mm). However, the cannula 52 may also have other lengths and outer cross sectional dimensions, depending upon the application. The cannula 52 may be formed from metal, plastic, and the like, and/or may be electrically active or inactive within the probe assembly 50, depending upon the manner in which electrical energy is to be applied.

The cannula 52 may coaxially surround the shaft 56 such that the shaft 56 may be advanced axially from or retracted axially into the lumen 54 of the cannula 52. Optionally, a handle 64 may be provided on the proximal end 58 of the shaft 56 to facilitate manipulating the shaft 56. The wires 62 may be compressed into a low profile when disposed within the lumen 54 of the cannula 52, as shown in FIG. 3. As shown in FIG. 4, the proximal end 58 of the shaft 56 or the handle 64 (if one is provided) may be advanced to deploy the wires from the lumen 54 of the cannula 52. When the wires 62 are unconfined outside the lumen 54 of the cannula 52, they may assume a relaxed expanded configuration. FIG. 4 shows an exemplary two-wire array including wires 62 biased towards a generally "U" shape and substantially uniformly separated from one another about a longitudinal axis of the shaft 56. Alternatively, each wire 62 may have other shapes, such as a "J" shape, and/or the array may have one wire 62 or more than two wires 62. The array may also have non-uniform spacing to produce an asymmetrical lesion. The wires 62 are preferably formed from spring wire, superelastic material, or other material, such as Nitinol, that may retain a shape memory. During use of the probe assembly 50, the wires 62 may be deployed into a target tissue region to deliver energy to the tissue to create a lesion.

Optionally, a marker (not shown) may be placed on the handle 64 and/or on the proximal end 58 of the shaft 56 for indicating a rotational orientation of the shaft 56 during use. The probe assembly 50 may also carry one or more radio-opaque markers (not shown) to assist positioning the probe assembly 50 during a procedure, as is known in the art. Optionally, the probe assembly 50 may also include a sensor, e.g., a temperature sensor and/or an impedance sensor (not shown), carried by the distal end of the shaft 56 and/or one or more of the wires 62.

Exemplary ablation devices having a spreading array of wires have been described in U.S. Pat. No. 5,855,576, the disclosure of which is expressly incorporated by reference herein.

It should be noted that the ablation devices 18, 20 are not necessarily limited to the probe assembly 50 shown in FIGS. 3 and 4, and that either or both of the ablation devices 18, 20 may be selected from a variety of devices that are capable of delivering ablation energy. For example, medical devices may also be used that are configured for delivering ultrasound energy, microwave energy, and/or other forms of energy for the purpose of ablation, which are well known in the art. Furthermore, the first and second ablation devices 18, 20 are not necessarily limited to the same type of devices. For example, the first ablation device 18 may deliver ultrasound energy while the second ablation device 20 may deliver radio-frequency energy. Also, the first and second ablation devices 18, 20 may have different sizes of arrays of wires 62, and/or different types or numbers of electrodes. For example, either of the first and second ablation devices 18, 20 may be an elongate member carrying a single electrode tip.

Figure 5A:
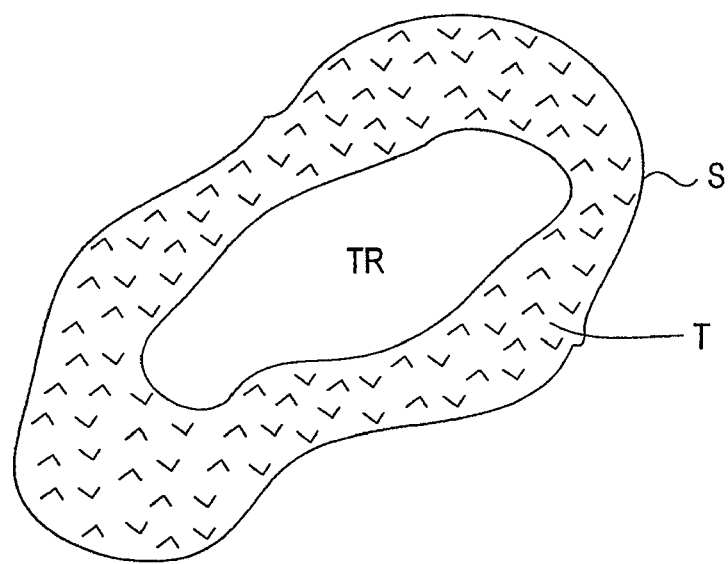
FIGS. 5A-5D are cross-sectional views, showing a method for treating tissue, in accordance with the present invention.
Figure 5B:
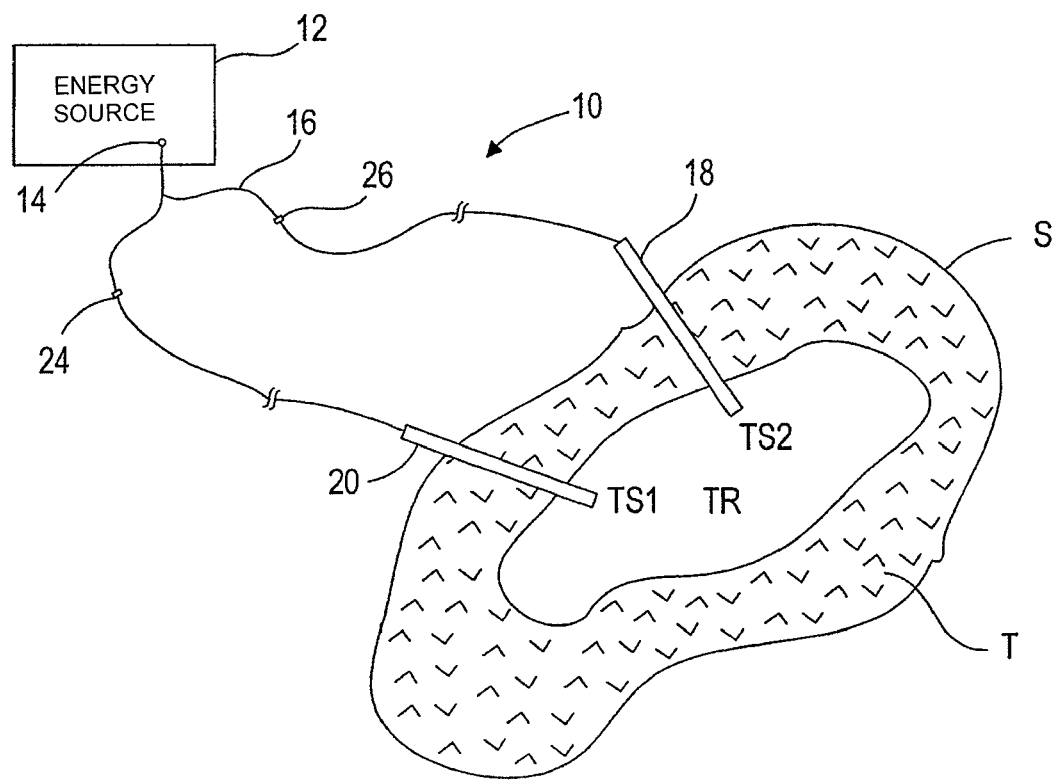

Referring now to FIGS. 5A-5D, the ablation system 10 may be used to treat a treatment region TR within tissue located beneath skin or an organ surface S of a patient. The tissue TR before treatment is shown in FIG. 5A. As shown in FIG. 5B, the cannulas 52 of the first and second ablation devices 18, 20 may be introduced into the treatment region TR, so that the respective distal ends of the cannulas 52 of the first and second ablation devices 18, 20 are located at first and second target sites TS1, TS2. This may be accomplished using any of a variety of techniques. In some cases, the cannulas 52 and shafts 56 of the respective ablation devices 18, 20 may be introduced into the target site TS percutaneously, i.e., directly through the patient's skin, or through an open surgical incision. In this case, the cannulas 52 may have a sharpened tip, e.g., a beveled or pointed tip, to facilitate introduction into the treatment region. In such cases, it is desirable that the cannulas 52 be sufficiently rigid, i.e., have sufficient column strength, so that the cannulas 52 may be accurately advanced through tissue.

In an alternative embodiment, the cannulas 52 may be introduced without the shafts 56 using internal stylets (not shown). Once the cannulas 52 are positioned as desired, the stylets may be exchanged for the shafts 56 that carry the wires 62. In this case, each of the cannulas 52 may be substantially flexible or semi-rigid, since the initial column strength of the apparatus 10 may be provided by the stylets. Various methods known in the art may be utilized to position the probe 50 before deploying the wires.

In a further alternative, one or more components or elements may be provided for introducing each of the cannulas 52 to the treatment region. For example, a conventional sheath and sharpened obturator (stylet) assembly (not shown) may be used to access the target site(s). The assembly may be positioned using ultrasonic or other conventional imaging. Once properly positioned, the obturator/stylet may be removed, providing an access lumen through the sheath. The cannula 52 and shaft 56 of each of the ablation devices 18, 20 may then be introduced through the respective sheath lumens so that the distal ends of the cannulas 52 of the first and second ablation devices 18, 20 advance from the sheaths into the target sites TS1, TS2.

Figure 5C:
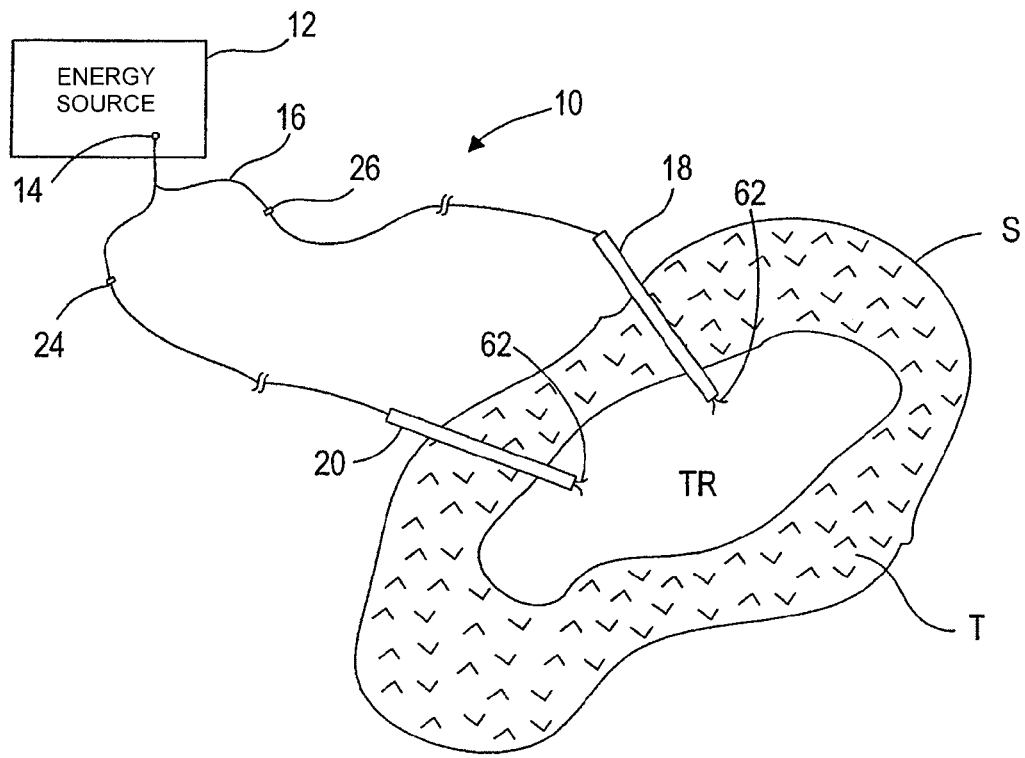
Figure 5D:
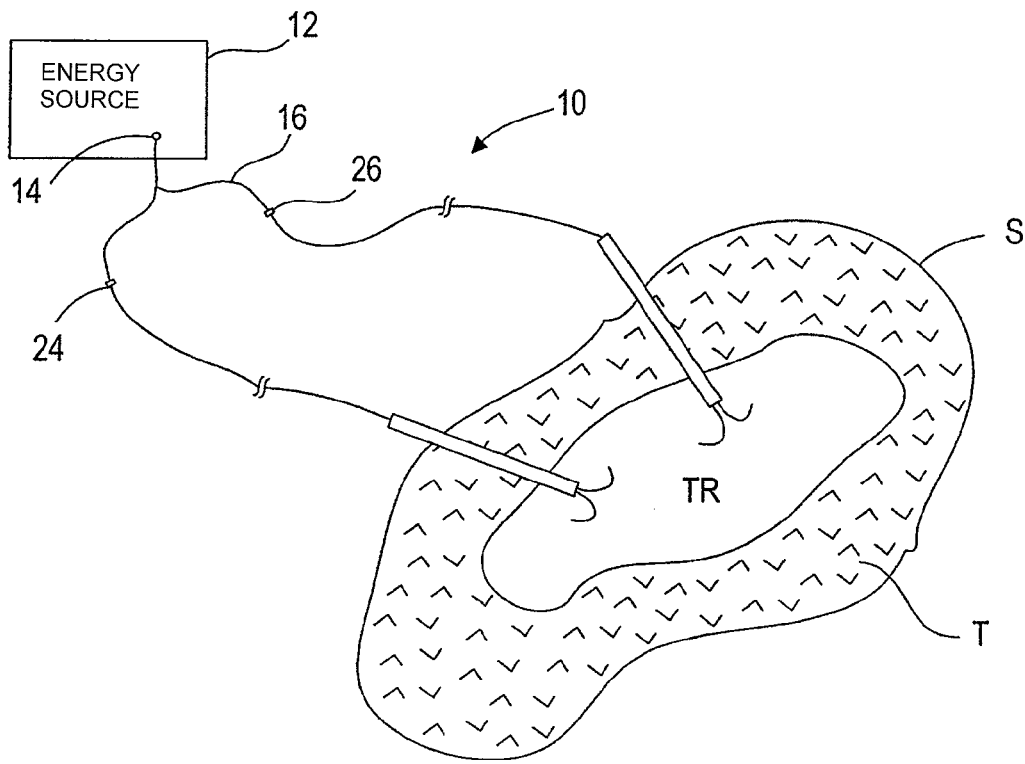

Turning to FIG. 5C, after the cannulas 52 of the ablation devices 18, 20 are properly placed, the shafts 56 of the respective ablation devices 18, 20 may be advanced distally, thereby deploying the arrays of wires 62 from the distal ends of the respective cannulas 52 into the target sites TS1, TS2. Preferably, the wires 62 are biased to curve radially outwardly as they are deployed from the cannulas 52. The shaft 56 of each of the ablation devices 18, 20 may be advanced sufficiently such that the wires 62 fully deploy to circumscribe substantially tissue within the target sites TS1, TS2 of the treatment region TR, as shown in FIG. 5D. Alternatively, the wires 62 may be only partially deployed or deployed incrementally in stages during a procedure.

If the generator 12 of the ablation system 10 includes only one output terminal 14, one or more connectors 16, described previously, may be used to couple the ablation devices 18, 20 to the output terminal 14. If the generator 12 includes more than one output terminals 14, the ablation devices 18, 20 may be coupled directly to the generator 12 without using the connector 16. Extension cables 28 may also be used to couple the ablation devices 18, 20 to the connector 16 or to the generator 12. The ablation devices 18, 20 may be coupled to the generator 12 in parallel with one another after the wires 62 of the respective ablation devices 18, 20 have been deployed. Alternatively, the wires 62 may be coupled to the generator 12 before the cannulas 52 are introduced to the treatment region, or at any time before the tissue is ablated. A neutral or ground electrode, e.g., an external electrode pad, may be coupled to the opposite terminal (not shown) of the generator 12 and coupled to the patient, e.g., the patient's skin, in a conventional manner.

Next, energy, preferably RF electrical energy, may be delivered from the generator 12 to the wires 62 of the respective ablation devices 18, 20, thereby substantially simultaneously creating lesions at the first and second target sites TS1, TS2 of the treatment region TR, respectively. Because the ablation devices 18, 20 are connected in parallel to the generator 12, as the impedance of tissue at one of the target sites TS1, TS2 increases, e.g., as the tissue is desiccated or otherwise treated, current may continue to flow to the other target site(s) to complete treatment of both target sites.

Simultaneously creating two or more lesions within a treatment region may substantially reduce the duration of an ablation procedure. In addition, using only a single generator 12 (or fewer generators than deployed ablation devices) may reduce the cost of equipment necessary to complete a procedure. When desired lesions at the first and second target sites TS1, TS2 of the treatment region TR have been created, the wires 62 of each of the ablation devices 18, 20 may be retracted into the respective lumens 54 of the cannulas 52, and the ablation devices 18, 20 may be removed from the treatment region TR. In many cases, two ablation devices 18, 20 may be sufficient to create a desired lesion. However, if it is desired to perform further ablation to increase the lesion size or to create lesions at different site(s) within the treatment region TR or elsewhere, the wires 62 of either or both of the ablation devices 18, 20 may be introduced and deployed at different target site(s), and the same steps discussed previously may be repeated.

Although an embodiment has been described with reference to placing ablation devices at different sites that are within a treatment region, the scope of the invention should not be so limited. In alternative embodiments, the ablation devices 18, 20 are disposed at different sites, each of which is associated with a treatment region. In such arrangement, separate tissues at different sites can be ablated simultaneously. In addition, it should be noted that the scope of the invention should not be limited to the ablation system 10 having two ablation devices. In alternative embodiments, the ablation system 10 can have more than two ablation devices.

Thus, although several preferred embodiments have been shown and described, it would be apparent to those skilled in the art that many changes and modifications may be made thereunto without the departing from the scope of the invention, which is defined by the following claims and their equivalents.

What is claimed:

1. A system for treating tissue within a tissue region using electrical energy, comprising:
   a source of electrical energy;
   a first ablation device comprising a first structure and a first electrode carried by the first structure, the first electrode coupled to the source of energy; and
   a second ablation device comprising a second structure and a second electrode carried by the second structure, the first and second ablation devices configured for substantially simultaneously creating first and second lesions at first and second sites, respectively, within a tissue region;
   wherein the first structure and the second structure are independently and laterally moveable relative to each other; and
   wherein the second electrode is coupled to the source of energy in parallel with the first electrode, such that as impedance of tissue at the first site increases, the second electrode continues to deliver current to tissue at the second site.

2. The system of claim 1, wherein the source of electrical energy comprises first and second terminals coupled in parallel to one another, and wherein the first ablation device is coupled to the first terminal, and the second ablation device is coupled to the second terminal.

3. The system of claim 2, wherein the source of electrical energy comprises first and second control circuits coupled to the first and second terminals, respectively, in parallel with one another, the first and second control circuits providing impedance feedback for the first and second terminals, respectively.

4. The system of claim 1, wherein the source of electrical energy comprises a terminal, and wherein the system further comprises a "Y" cable coupled between the first and second ablation devices and the terminal.

5. The system of claim 4, wherein each of the first structure and the second structure comprises an elongated probe member configured to be placed into contact with tissue.

6. The system of claim 1, wherein the first and the second ablation devices have substantially the same configuration.

7. The system of claim 1, wherein the first ablation device comprises a first array of wires deployable from a first cannula, the first electrode being one of the wires of the first array, and the second ablation device comprises a second array of wires deployable from a second cannula, the second electrode being one of the wires of the second array.

8. A system for treating tissue within a tissue region using electrical energy, comprising:
   a source of electrical energy;
   a first ablation device comprising a first structure and a first electrode carried by the first structure, the first electrode coupled to the source of energy; and a second ablation device comprising a second structure and a second electrode carried by the second structure, the second electrode coupled to the source of energy in parallel with the first electrode, whereby the first and second ablation devices can substantially simultaneously create first and second lesions, respectively, within a tissue region;

wherein the first structure and the second structure are independently and laterally moveable relative to each other.

9. The system of claim 8, further comprising a ground electrode coupled to the source of energy opposite the first and second electrodes.

10. The system of claim 8, wherein the source of electrical energy comprises first and second terminals coupled in parallel to one another, and wherein the first ablation device is coupled to the first terminal and the second ablation device is coupled to the second terminal.

11. The system of claim 10, wherein the source of electrical energy comprises first and second control circuits coupled to the first and second terminals, respectively, in parallel with one another, the first and second control circuits providing impedance feedback for the first and second terminals, respectively.

12. The system of claim 8, wherein the source of electrical energy comprises a terminal, and wherein the system further comprises a "Y" cable coupled between the first and second ablation devices and the terminal.

13. The system of claim 8, wherein the source of electrical energy comprises circuitry for determining impedance between a ground electrode and one of the first and second electrodes.

14. The system of claim 8, The system of claim 1, wherein the first ablation device comprises a first array of wires deployable from a first cannula, the first electrode being one of the wires of the first array, and the second ablation device comprises a second array of wires deployable from a second cannula, the second electrode being one of the wires of the second array.

15. The system of claim 8, wherein each of the first structure and the second structure comprises an elongated probe member configured to be placed into contact with tissue.

16. The system of claim 8, wherein the first and the second ablation devices have substantially the same configuration.

17. A method for creating a lesion within a tissue region, the method comprising:
coupling a first array of electrodes and a second array of electrodes to a source of energy;
percutaneously inserting the first array of electrodes via a first path into a first site within a tissue region;
percutaneously inserting the second array of electrodes via a second different path into a second site within the tissue region, the second array of electrodes being coupled in parallel with the first array of electrodes; and
simultaneously using the first and the second arrays of electrodes to respectively generate first and second lesions at the first and the second sites.

18. The method of claim 17, wherein the second array of electrodes continues to deliver current to the second site as impedance of tissue at the first site increases.

19. The method of claim 17, wherein the first and the second arrays of electrodes are deployed from cannulae into the first and second sites, respectively.

20. The method of claim 17, wherein the first and second arrays of electrodes are coupled to a source of electrical energy by connecting the first array of electrodes to a first output terminal of the source of electrical energy and connecting the second array of electrodes to a second output terminal of the source of electrical energy.

21. The method of claim 17, wherein the first and second arrays of electrodes are coupled to a source of electrical energy by coupling one end of a connector to a terminal of the source of electrical energy, and coupling parallel ends of the connector to the first and second arrays of electrodes.

22. The method of claim 17, wherein the tissue region comprises a liver.

23. The method of claim 17, wherein the first and the second lesions at least partially overlap each other.

24. The method of claim 17, wherein the first array of electrodes is introduced into the first site from a first cannula, and the second array of electrodes are introduced into the second site from a second cannula.

* * * * *